United States Patent
Wiek et al.

(10) Patent No.: US 8,394,334 B2
(45) Date of Patent: Mar. 12, 2013

(54) DEVICE FOR FURTHER PROCESSING A FLUID MATERIALS

(75) Inventors: Hans-Dieter Wiek, Hochdorf (DE); Uwe Mohn, Schelklingen (DE)

(73) Assignee: Kaltenbach & Voigt GmbH, Biberach (DE)

( * ) Notice: Subject to any disclaimer, the term of this patent is extended or adjusted under 35 U.S.C. 154(b) by 319 days.

(21) Appl. No.: 12/600,428

(22) PCT Filed: May 16, 2008

(86) PCT No.: PCT/EP2008/003967
§ 371 (c)(1),
(2), (4) Date: Dec. 23, 2009

(87) PCT Pub. No.: WO2008/138645
PCT Pub. Date: Nov. 20, 2008

(65) Prior Publication Data
US 2010/0151415 A1    Jun. 17, 2010

(30) Foreign Application Priority Data

May 16, 2007 (DE) .......................... 10 2007 022 946

(51) Int. Cl.
*A61L 2/00* (2006.01)
*A61L 9/00* (2006.01)

(52) U.S. Cl. ......... 422/300; 422/292; 422/295; 422/297

(58) Field of Classification Search .................. 422/292, 422/300, 295, 297
See application file for complete search history.

(56) References Cited

U.S. PATENT DOCUMENTS

| | | | |
|---|---|---|---|
| 5,178,308 A * | 1/1993 | Endre ........................... | 224/435 |
| 5,305,900 A * | 4/1994 | Maguire et al. ............... | 215/245 |
| 6,217,329 B1 * | 4/2001 | Eibofner et al. ............... | 433/104 |
| 7,032,364 B2 * | 4/2006 | Yoshida et al. ................ | 53/432 |
| 2001/0037970 A1 * | 11/2001 | Farley ............................ | 210/435 |
| 2002/0027142 A1 * | 3/2002 | Klein .............................. | 220/737 |
| 2007/0119980 A1 * | 5/2007 | Somerfield et al. ............ | 239/302 |

FOREIGN PATENT DOCUMENTS

| | | |
|---|---|---|
| DE | 19913945 A1 | 9/2000 |
| EP | 1665999 A2 | 6/2006 |

OTHER PUBLICATIONS

International Search Report for PCT/EP2008/003967 dated May 28, 2009.

* cited by examiner

*Primary Examiner* — Regina M. Yoo
(74) *Attorney, Agent, or Firm* — Marshall, Gerstein & Borun LLP

(57) ABSTRACT

A device for further processing a fluid material, particularly a care device for medical or dental tool holders, the material being stored in a tank under pressure, the device having a coupling fixture having an adapter forming a screw connection to the tank under pressure, the adapter of the coupling fixture being pivotally supported.

19 Claims, 4 Drawing Sheets

DEVICE FOR FURTHER PROCESSING A FLUID MATERIALS

BACKGROUND OF THE INVENTION

1. Field of the Invention

The present invention relates to a device according to the preamble of claim 1 intended for further processing a fluid agent, wherein the agent is stored in a pressurized container. In particular, the present invention relates to a device for maintaining medical or dental handpieces.

2. Related Technology

A maintenance device such as this is known, for example, from DE 199 13 945 A1, which belongs to the applicant. It is used, in particular, to clean and to maintain the drive channels, and also the drive elements rotatably mounted therein, of dental handpieces. Here the handpieces are coupled to corresponding connections, via which cleaning and care agents are fed through the various channels of the tubular handpieces. In particular, the care agent supplied last in this case is used to protect the individual components against excessive wear during use.

The manufacturer generally provides the care agent used for maintaining such medical or dental handpieces in the form of spray cans. These cans contain the care agent in pressurized form and make it available when required, wherein the device provides a corresponding coupling apparatus with an adapter for connection to the spray can or generally the pressurized storage container.

The care agents used for carrying out such maintenance measures are usually highly flammable. Since the containers are also pressurized, care must be taken to ensure that there is a reliable connection between the storage container for the care agent and the maintenance device. Despite various types of solutions, the optimum connection to date has still proved to be a screw connection. However, this has the associated disadvantage that the removal and reinsertion of a storage container is complicated, or at least means that it is necessary to make it easier to access the coupling apparatus, for example by making the housing larger.

SUMMARY OF THE INVENTION

The invention makes it possible to produce a reliable coupling between a storage container for a care agent and a corresponding device, while at the same time making handling easier as compared with solutions known to date.

Accordingly, the invention provides a device for further processing a fluid agent, in particular a maintenance device for medical or dental handpieces, which agent is stored in a pressurized container, wherein the device has a coupling apparatus with an adapter for forming a screw connection to the pressurized container, wherein the adapter of the coupling apparatus is pivotably mounted.

The solution according to the invention is, in turn, initially based on the concept of designing the coupling apparatus in such a way that it is possible to form a screw connection to the pressurized container via a corresponding adapter. According to the invention, however, the coupling apparatus is designed in such a way that the adapter is pivotably mounted.

Accordingly, the invention proposes a device for further processing a fluid agent, in particular a maintenance device for medical or dental handpieces, wherein the agent is stored in a pressurized container, the device has a coupling apparatus with an adapter for forming a screw connection to the pressurized container and wherein, according to the invention, the adapter of the coupling apparatus is pivotably mounted.

The pivotable mounting of the adapter for forming the screw connection to the pressurized container makes it easier to change a storage container for a corresponding care agent since, for the screwing-in and unscrewing operations, the adapter and therefore the container to be fastened to it can be positioned in such a way that it is easier to access the container. In particular, it may be provided that the adapter of the coupling apparatus is pivotable between an operating position, in which the container is arranged completely inside a housing of the device, and a maintenance position, wherein at least part of the storage container protrudes out of the device housing in the maintenance position. In this case, it may be provided, in particular, that the coupling apparatus is provided with latching means which firstly define the operating position and secondly define the maintenance position.

The solution according to the invention is therefore distinguished in that firstly it is possible to produce an extremely reliable connection between the storage container and the device, and secondly it is easier to insert and remove the storage container. Overall, this improves the handling of the device.

BRIEF DESCRIPTION OF THE DRAWINGS

The invention will be explained in more detail below with reference to the appended drawings, in which.

DETAILED DESCRIPTION

Figure 1:
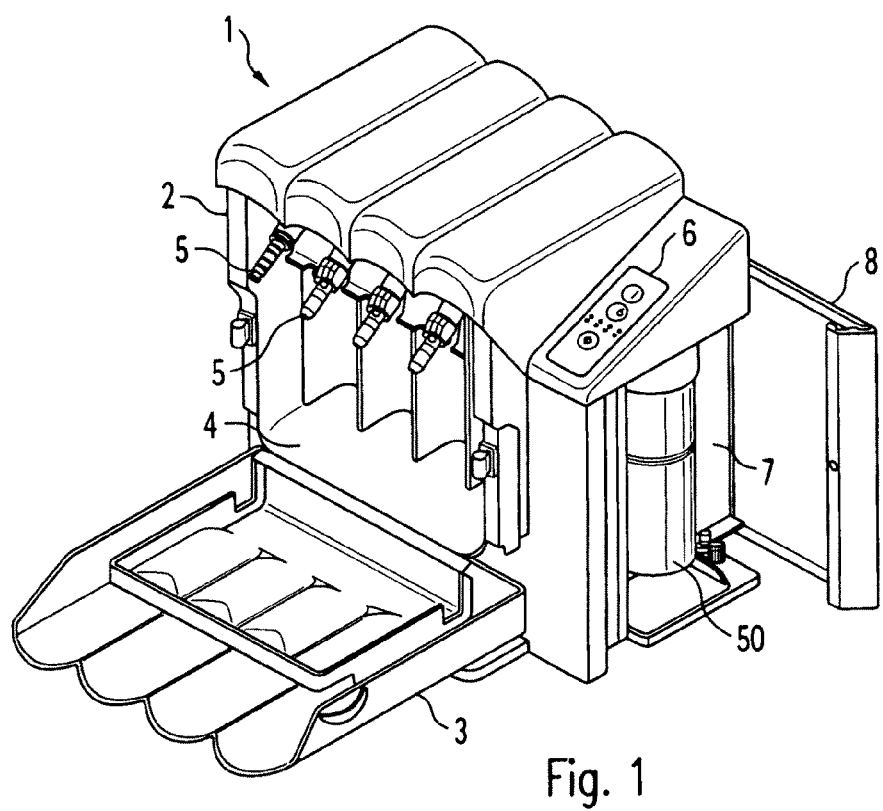
FIG. 1 shows a perspective view of a device according to the invention for maintaining medical or dental handpieces.

FIG. 1 shows a maintenance device which is designated generally by the reference symbol 1, the individual parts and assemblies of which are integrated in a housing 2. This housing has a substantially cuboidal form, the front side being provided with a first swing door 3 via which access can be gained to a maintenance space 4. FIG. 1 shows the maintenance device 1 with the door 3 open.

The maintenance space 4 is used to accommodate medical or dental handpieces which are to be cleaned and maintained, this being done by forming a plurality of insert connection parts 5 within the maintenance space 4, it being possible to attach the handpieces onto these connection parts. The insert connection parts 5 are formed with corresponding supply lines via which cleaning and/or care agents can be introduced into the handpieces in order to maintain them. With respect to the special procedure for cleaning and maintaining the handpieces, reference is made to DE 199 13 945 A1, which has already been mentioned above. The device 1 is operated using a control panel 6 formed on the upper side of the housing 2.

The care agent fed through the handpieces in order to complete the cleaning and maintenance process, in particular, is provided by an exchangeable storage container in the form of a pressurized can 50. As shown in the illustration in FIG. 1, a further accommodating space 7, which is accessible via a further door 8 on the side, is formed in the housing 2 in order to accommodate the can 50. A special coupling apparatus, which is explained in more detail below, is used to connect the can 50 to the device 1, so that the care agent can be removed during operation of the device 1.

Figure 2:
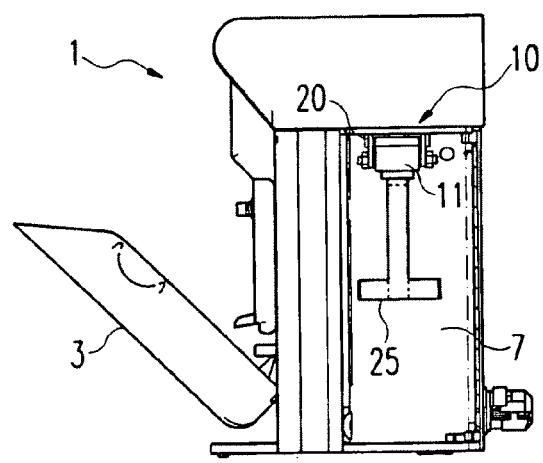
FIG. 2 shows a side view of the device shown in FIG. 1.
Figure 3:
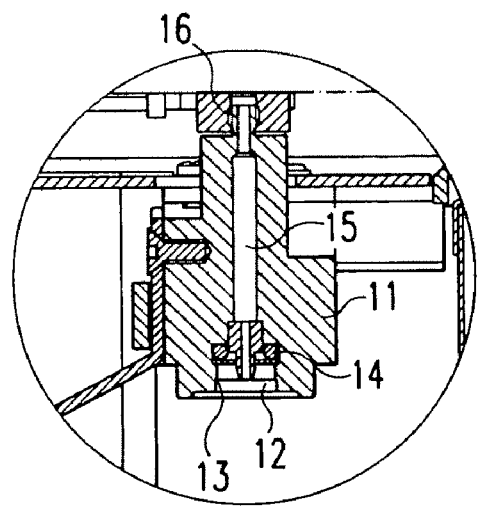
FIGS. 3 to 6 show different views of the coupling apparatus with the pivotably mounted adapter.

The care agent normally used for cleaning and maintaining medical or dental handpieces is flammable, and therefore a reliable connection should be produced when coupling the pressurized can 50 to the device 1. The coupling apparatus provided for this purpose, which is shown, for example, in the side view in FIG. 2 and is designated by the reference symbol 10, accordingly has an adapter 11 which is designed to form a screw connection to the pressurized can 50. The problem arises here that the can 50 must be fitted to the adapter 11 in a suitable manner; in the case of embodiments known to date, this has led to relatively complicated handling. In particular, in the position shown in FIG. 1, it is only possible with difficulty to grip the can 50 and screw it in and unscrew it, since the space in the accommodating space 7 is very restricted. In order accordingly to make handling easier, the coupling apparatus 10 has a special design, which is explained below.

The special feature of the coupling apparatus 10 shown in more detail in FIGS. 3 to 7 is that it has a pivotably mounted adapter 11. In accordance with the illustrations, the underside of the adapter 11 is provided with an insertion opening 12 for the valve connection of the pressurized can 50, this opening being provided with an internal thread 13 in order to form a screw connection to the can 50. An O-ring 14, which provides an additional seal, is arranged on the bottom of the insertion opening 12 in order ultimately to reliably produce a pressure-tight connection to the can 50. A passage line or bore 15 extends through the adapter 11 and, at its upper end, ends at a connection piece 16 for a media line via which the corresponding care agent can then ultimately be supplied to the maintenance device 1. This passage line 15 may optionally be opened or closed via a shut-off valve 17 which can be activated using a stop-cock or lever 18 formed on the front side of the adapter 11; this further increases the operational reliability.

Figure 4:
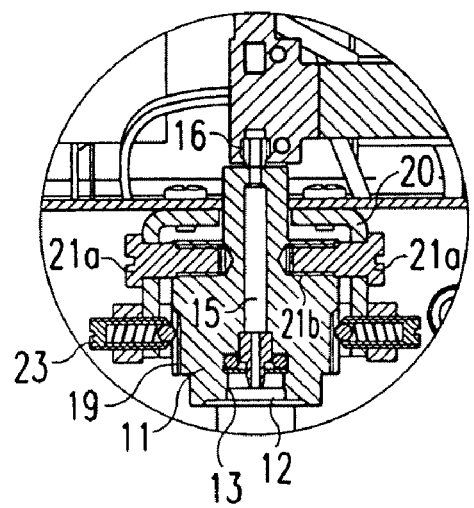
Figure 5:
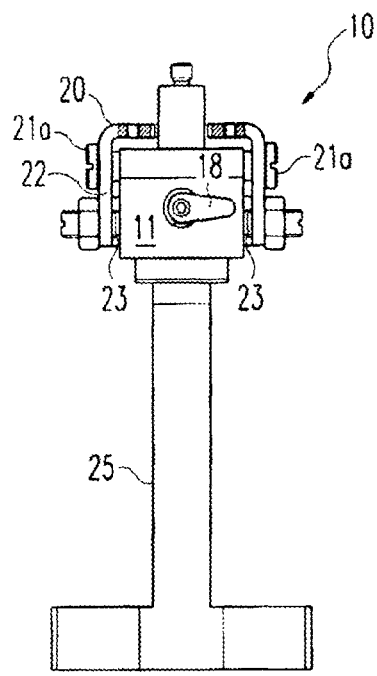
Figure 6:
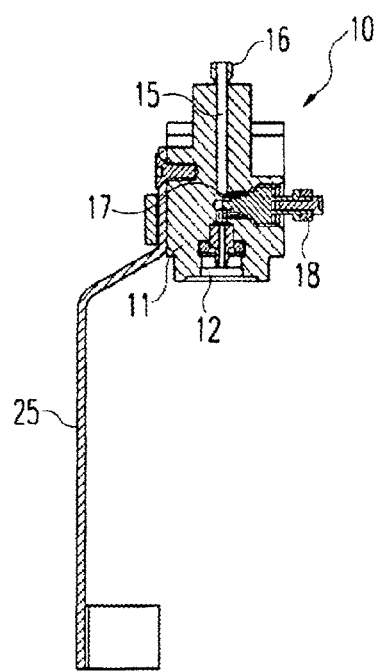
Figure 7:
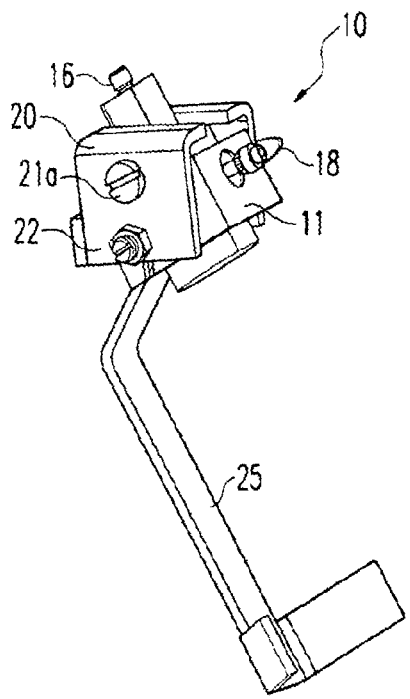
FIG. 7 shows the adapter pivoted into the maintenance position.

In accordance with the sectional illustration in FIG. 4, the adapter 11 is mounted on a clasp-shaped holder 20, two lateral pins 21a engaging in corresponding openings or recesses 21b in the adapter 11. These pins 21a, which are fastened to lateral arms 22 of the holder 20, define a pivot axis which makes it possible to pivot the adapter 11 between two different positions. Latching devices which define two different pivoted positions of the adapter 11 are formed by grooves 19 formed on the outside of the adapter 11 and by pins 23 which interact with these grooves 19 and are fastened to the undersides of the clasp-like holding element 20. In a first position, the adapter 11 is oriented vertically. This position corresponds to an operating position in which the spray can 50 is arranged completely inside the accommodating space 7, as shown in FIG. 1. By contrast, the maintenance position shown in FIG. 7 is distinguished by the fact that the adapter 11 is pivoted by an angle of about 30° to 45° with respect to the holding element 20. In this case, a guide 25, which protrudes from the adapter toward the underside, is pivoted out of the housing.

Figures 8, 9:
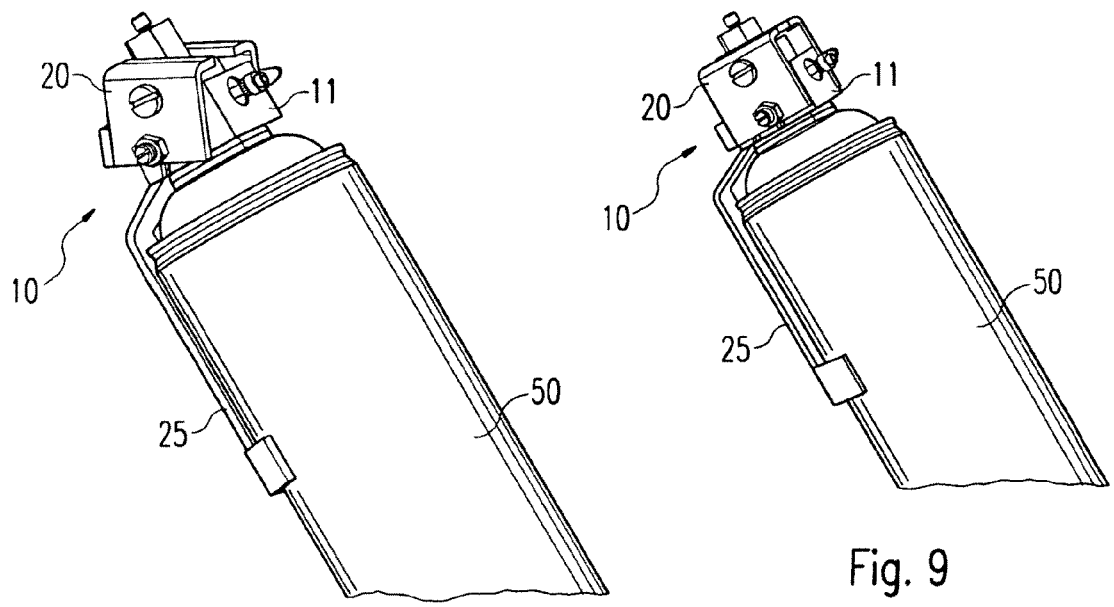
FIGS. 8 and 9 show arrangements of a care agent can, connected to the adapter, in the two different pivoted positions.

In accordance with the illustrations in FIGS. 8 and 9, where FIG. 8 shows the maintenance position and FIG. 9 shows the operating position, at least the lower end of the can 50 is also guided out of the housing 2 of the maintenance device 1 in the maintenance position. The can 50 may therefore be placed obliquely from the underside on the adapter 11 latched in the maintenance position and be screwed thereto. It is easy to carry out this process since it is easy to grip the can 50 when the adapter 11 is pivoted laterally and therefore the can protrudes. Once the screw connection has been produced between the can 50 and the adapter 11, the latter is pivoted into the operating position and the can is therefore inserted completely into the accommodating space 7, in accordance with the illustration in FIG. 1.

The advantage of this special refinement is that it is very simple to exchange the can while simultaneously being able to produce a reliable and, in particular, pressure-tight connection between the adapter and the can by way of a screw connection. As a result, the device is easy to handle and operation is highly reliable.

The invention claimed is:

1. A device for processing a fluid agent, which agent is stored in a pressurized container, the device comprising:
a coupling apparatus with an adapter having an insertion opening with an internal thread on a bottom of the adapter, the insertion opening forming a screw connection and a passage extending through the adapter from the insertion opening to an upper connection piece for a media line, and a holder for coupling the adapter to the device;
wherein the adapter is pivotably mounted to the holder, the adapter having a pivot axis that is substantially perpendicular to a longitudinal axis of the adapter.

2. The device as claimed in claim 1, wherein the adapter of the coupling apparatus is pivotably connected to the holder and movable between an operating position and a maintenance position.

3. The device as claimed in claim 2, wherein the coupling apparatus comprises a latch that firstly defines the operating position and secondly defines the maintenance position.

4. The device as claimed in claim 2, further comprising a pressurized container coupled to the adapter in the maintenance position that protrudes out of a housing of the device.

5. The device as claimed in claim 2, further comprising a pressurized container coupled to the adapter in the operating position that is arranged vertically in the device.

6. The device as claimed in claim 1, further comprising an accommodating space for the pressurized container, accessible via a door.

7. The device as claimed in claim 1, wherein the holder is a clasp-like holder.

8. The device as claimed in claim 1, further comprising shut-off means located on the adapter for optionally opening or closing off a supply line that leads from the pressurized container to the device.

9. The device as claimed in claim 1, wherein the device is disposed in a maintenance device for medical or dental handpieces.

10. A maintenance and cleaning device for dental instruments, the device comprising:
a housing having a first door for accessing a maintenance space within the housing, the maintenance space including a plurality of insert connection parts for attaching to dental handpieces, and a second door for accessing an accommodating space for an exchangeable storage container;
a coupling apparatus for coupling the exchangeable storage container to the device, the coupling apparatus including an adapter having a bottom insertion opening forming a threaded connection for threadably connecting the adapter to the exchangeable storage container, the adapter including a passage line extending from the bottom insertion opening to an upper connection piece for a media line, and a clasp-shaped holder attached to the housing, wherein the adapter is pivotably attached to the clasp-shaped holder, the adapter pivoting about an axis that is substantially perpendicular to a longitudinal axis of the adapter.

11. The device of claim 10, further comprising a latching device for holding the adapter in a first position or a second position.

12. The device of claim 11, wherein the latching device includes a groove on the adapter and a pin on the clasp-shaped holder.

13. The device of claim 10, wherein the adapter is pivotable between about 30° and about 45° relative to the clasp-shaped holder.

14. The device of claim 10, further comprising a guide that protrudes from the adapter.

15. The device of claim 14, wherein the guide is pivotable with the adapter relative to the clasp-like holder.

16. The device of claim 10, wherein the passage line is substantially parallel to the longitudinal axis of the adapter.

17. The device of claim 10, further comprising a shut-off valve attached to the adapter for selectively closing or opening the passage line.

18. The device of claim 17, further comprising a lever attached to the shut-off valve.

19. The device of claim 10, wherein the clasp-shaped holder includes a pair of lateral arms and a lateral pin extending through an opening in each arm, the lateral pins defining a pivot axis of the adapter.

* * * * *

UNITED STATES PATENT AND TRADEMARK OFFICE
CERTIFICATE OF CORRECTION

PATENT NO.        : 8,394,334 B2               Page 1 of 1
APPLICATION NO.   : 12/600428
DATED             : March 12, 2013
INVENTOR(S)       : Wiek et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 381 days.

Signed and Sealed this
First Day of September, 2015

Michelle K. Lee
*Director of the United States Patent and Trademark Office*